US012390106B2

United States Patent
Wang

(10) Patent No.: US 12,390,106 B2
(45) Date of Patent: Aug. 19, 2025

(54) EYE IMAGE ANALYSIS SYSTEM BASED ON ADDITIONAL FLOODLIGHT PROJECTION DEVICE AND OPHTHALMIC SLIT LAMP

(71) Applicant: CHONGQING KANGHUA RUIMING SCIENCE TECHNOLOGY CO., LTD, Chongqing (CN)

(72) Inventor: Yi Wang, Chong Qing (CN)

(73) Assignee: CHONGQING KANGHUA RUIMING SCIENCE TECHNOLOGY CO., LTD, Chongqing (CN)

( * ) Notice: Subject to any disclaimer, the term of this patent is extended or adjusted under 35 U.S.C. 154(b) by 751 days.

(21) Appl. No.: 17/612,853

(22) PCT Filed: May 11, 2020

(86) PCT No.: PCT/CN2020/089585
§ 371 (c)(1),
(2) Date: Nov. 19, 2021

(87) PCT Pub. No.: WO2020/238593
PCT Pub. Date: Dec. 3, 2020

(65) Prior Publication Data
US 2022/0218200 A1    Jul. 14, 2022

(30) Foreign Application Priority Data
May 24, 2019    (CN) .......................... 201910437760.1

(51) Int. Cl.
A61B 3/135 (2006.01)
A61B 3/00 (2006.01)
(Continued)

(52) U.S. Cl.
CPC ............. *A61B 3/135* (2013.01); *A61B 3/0025* (2013.01); *A61B 3/132* (2013.01); *G06T 7/0012* (2013.01);
(Continued)

(58) Field of Classification Search
CPC ....... A61B 3/135; A61B 3/0025; A61B 3/132; A61B 3/107; A61B 3/14; A61B 3/18;
(Continued)

(56) References Cited

U.S. PATENT DOCUMENTS 5,954,711 A *  9/1999  Ozaki ..................... A61F 9/008
606/6
2005/0195360 A1 *  9/2005  Akita ..................... A61B 3/135
351/212
(Continued)

*Primary Examiner* — Bumsuk Won
*Assistant Examiner* — Rahman Abdur
(74) *Attorney, Agent, or Firm* — Tutunjian & Bitetto, P.C.

(57) ABSTRACT

An eye image analysis system based on an additional floodlight projection device and an ophthalmic slit lamp, comprising an ophthalmic slit lamp microscope detector, the additional floodlight projection device, an image acquisition device, and an image analysis device. The additional floodlight projection device is detachably and rotatably connected to the ophthalmic slit lamp microscope detector and used for forming a floodlight map graph with special reticulate patterns on the cornea to be detected. The image acquisition device is used for performing, optical image collection on the floodlight map graph to form an examination data packet and sending the examination data packet to the image analysis device, and the image analysis device is used for performing processed processing, digitized filtering comparison and measurement, and pathological analysis on the obtained examination data packet to obtain a pathological examination result.

3 Claims, 3 Drawing Sheets

(51) Int. Cl.
*A61B 3/13* (2006.01)
*G06T 7/00* (2017.01)

(52) U.S. Cl.
CPC ............... *G06T 2207/10056* (2013.01); *G06T 2207/30041* (2013.01)

(58) Field of Classification Search
CPC ......... G06T 7/0012; G06T 2207/10056; G06T 2207/30041
USPC ....................................................... 351/214
See application file for complete search history.

(56) References Cited

U.S. PATENT DOCUMENTS

| | | | |
|---|---|---|---|
| 2016/0038024 A1* | 2/2016 | Zhou | A61B 3/113 351/206 |
| 2019/0059720 A1 | 2/2019 | Kubota | |

* cited by examiner

EYE IMAGE ANALYSIS SYSTEM BASED ON ADDITIONAL FLOODLIGHT PROJECTION DEVICE AND OPHTHALMIC SLIT LAMP

TECHNICAL FIELD

The present invention relates to the technical field of ophthalmic medical equipment, specifically to an eye image analysis system based on an additional floodlight projection device and an ophthalmic slit lamp.

BACKGROUND TECHNOLOGY

As the most widely used pathological examination equipment in ophthalmic medicine, the eye is based on the following two basic equipment structural devices, namely the slit light projection device and binocular microscopy observation device (or digital imaging recording device), irradiation the depth of the eye with slit strong light at the appropriate angle and width, to achieve binocular high times micro detailed observation and obtain pathological images.

However, the pathological observation of the surface body condition of the eyeball cornea is a function that this kind of ophthalmic special medical equipment does not have. Therefore, the ophthalmic slit lamp microscope detector, as a platform with micro observation ability, still has the space to expand and utilize its function.

Clinical requirements for special pathological observation of the cornea based on ophthalmology, The invention develops a special additional device for the principle of mesh imaging required for the surface shape and condition of the eye, Without affecting the function of the original equipment, Can be based on the ophthalmic slit lamp microscope detector as a platform, A variety of mesh mapping maps with special purpose design, The realization lies in the comprehensive functional expansion of the pathological observation of both the internal depth state and the surface shape of the ophthalmic slit lamp microscope detector; and, A higher-resolution corneal surface mesh mapping image can be obtained with the binocular microscope observation device and the digital image acquisition function, Can use its independent and unique system professional digital image analysis process, Intelligent enhancement for the pathological observation means and judgment method under the principle of corneal surface deformation.

CONTENT OF INVENTION

In view of this, the object of the present invention is to provide an eye image analysis system based on an ophthalmic slit lamp and an additional floodlight projection device to improve and expand the professional technical means of this type of ophthalmic pathology examination device, and a variety of special purposes can be projected on the corneal surface of the eye, thus directly using the binocular microscope device of the ophthalmic slit lamp microscope detector and corresponding pathological analysis.

To achieve the above purpose, the technical schemes adopted in the present invention are as follows:

An eye image analysis system based on an additional floodlight projection device and an ophthalmic slit lamp, including an ophthalmic slit lamp microscope detector, key to further comprising an additional floodlight projection device, an image acquisition device, and an image analysis device, wherein:

The removable rotation of the additional floodlight projection device is attached to the slit lamp microscope detector for forming a floodlight map graph with a special mesh pattern on the surface of the cornea to be detected;

The image acquisition device is used for optical image acquisition of an optical map graph formed on the detected corneal surface through the optical aperture, forming an inspection data packet, and transmitting to the image analysis device;

The image analysis device is used to process the obtained inspection data package, data filtering contrast measurement, pathological analysis to obtain the pathological examination results.

Further, the additional floodlight projection device comprises a flood projection structure and a projection light source attached to the ophthalmic slit lamp microscope detector object with an arm attached at a free end rotated attached to the ophthalmic slit lamp microscope detector, which may image a required projection pattern for ophthalmic examination into the floodlight map graph with a special mesh on the surface of the cornea to be detected.

Further, the center of the projection structure opens an optical aperture along its axis, Further, the projection pattern may be quickly replaced by the positioned slide pattern insert.

Further, the projection light source adopts a reflective color filter universal light source in an annular arrangement and collinear with the centerline of the projection structure.

Further, a result printing device which can print the results of computer software assisted analysis obtained from the independent digital image acquisition processing analysis system.

The remarkable effect of the present invention are:
1. The present invention is based on an ophthalmic slit lamp microscope detector, and the original function of the ophthalmic slit lamp microscope detector is not changed and limited, realizing the pathological function of the internal depth and surface shape;
2. The additional floodlight projection device is designed to swing completely in the front area of the ocular ophthalmic slit lamp microscope detector to be moved to a non-working position without use, without hindering the normal use of the ophthalmic slit lamp microscope projector with high convenience of use;
3. can not only directly observe a variety of optical mesh mapping graphs with special purpose designs on the corneal surface.

APPENDIX DESCRIPTION

SPECIFIC IMPLEMENTATION MODE

The specific embodiment of the working principles and the present invention are further explained in detail in combination with the drawings.

Figure 1:
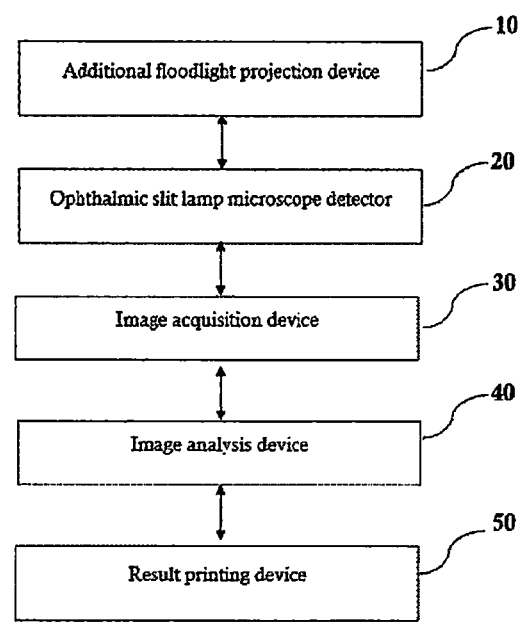
FIG. 1 is a principle block diagram of the present invention.

As shown in FIG. 1, an eye image analysis system based on an ophthalmic slit lamp and an additional floodlight projection device includes an ophthalmic slit lamp microscope detector 20, an image acquisition device 30, an independent image analysis device 40, and a result printing device 50, wherein:

The removable rotation of the additional floodlight projection device 10 is connected to the ophthalmic slit lamp microscope detector 20 for forming a floodlight map graph with a special mesh on the surface of the cornea to be detected;

The image acquisition device 30 is used for optical image acquisition of detecting an optical map graph formed on the surface of the cornea through an optical aperture, forming an inspection data packet, and transmitting it to the image analysis device 40;

The image analysis device 40 is used to perform process processing, data filtering comparison measurement, pathological analysis to obtain pathological examination results; wherein the process processing includes filtering and strengthening the graphical data in the inspection package; the data filtering comparison measurement function refers to graphic alignment screening and data measurement with the graphics stored in the standard graphics library within the image analysis device 40 to extract the drawing with pathological changes and then provide a basis for pathological analysis;

The result printing device 50 is used to print the pathological examination results obtained from the image analysis device 40.

In this example, the ophthalmic slit lamp microscope detector 20, the image acquisition device 30, and the result printing device 50 may all be devices in the prior art, and the specific structure may not be described here.

The image combination analysis system of the present invention is based on an optical microscope structure of a slit lamp, Project the images, figures, and lines projected from the internal light source of the additional floodlight projection device 10 on the corneal surface of the eye, Image images, figures, line shape projections on the corneal surface, Observation of different magnification (6×, 10×, 15×, 25.6×, 40×) was performed using the optical microscope of the ophthalmic slit lamp microscope detector 20 itself, The image acquisition device 30 then digitally takes a floodlight map graph detecting the formation of the corneal surface, Realize the optical image acquisition, After forming the inspection packet, it is sent to the image analysis device 40 for process processing, data filtering contrast determination, and pathological analysis, Pathological examination results are obtained and printed by the result printing device 50.

Figure 2:
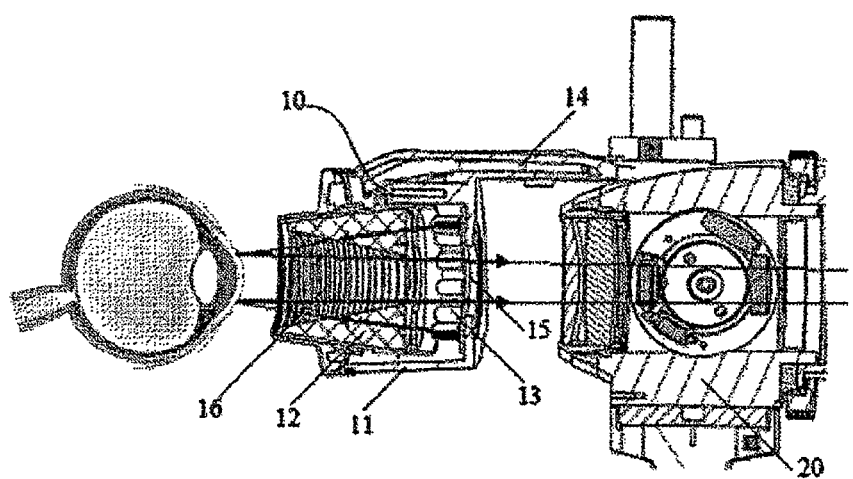
FIG. 2 is a schematic structural diagram of the additional floodlight projection device.
Figure 3:
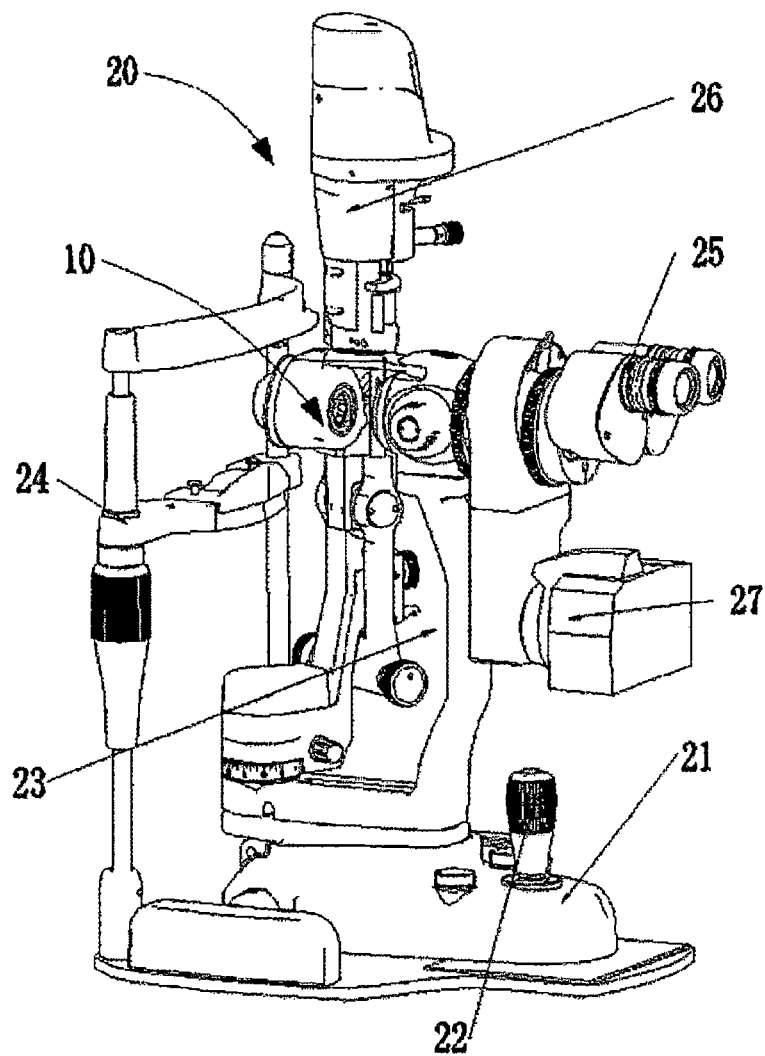
FIG. 3 is a schematic diagram of the use status of the additional floodlight projection device.

Refer to Supplementary FIG. 2 and Supplementary FIG. 3, The additional floodlight projection device is located between the eye and the ophthalmic slit lamp microscope detector 20 when use, It includes an outer cover 11, and a projection structure 12 and a projection light source 13 disposed within the outer cover 11; Arms 14 are fixed to the side wall of the outer cover 11, The free end of the arm 14 is used for rotational connection to the ophthalmic slit lamp microscope detector 20, A mounting chamber 15 is provided at the center of the outer cover 11, The projection light source 13 is embedded in the inner wall of the mounting chamber 15, The projection structure 12 is provided in the mounting cavity 15 and is provided close to the projection light source 13, The projection structure 12 is disposed close to the ophthalmic slit lamp microscope detector 20, The projection light source 13 forms a pan-optical projection channel with the projection structure 12 along the axis of the through hole 15.

In FIG. 2, the center of the projection structure 12 is axially provided with an optical channel 16, the projection pattern of which can be rapidly replaced by a positioned slide pattern insert.

In this example, the projection light source 13 adopts a reflective color filter universal light source, which is arranged annular and collinear with the centerline of the projection structure. Moreover, the projection light source 13 is a flexible replacement structure.

The projection light source has a hole in the middle of the projection light source 13 to facilitate the optical microscope of the ophthalmic slit lamp microscope detector 20 to observe the projection to the corneal surface of the eye. Through digital image acquisition of the eye optical mapping graph, an independent intelligent procedural professional pathological analysis can be performed.

The additional floodlight projection device 10 acts only as an additional device and does not affect the main function and other additional functions of the slit lamp, except the increased function of the ophthalmic slit lamp microscope detector 20, according to FIG. 2 designed to swing in the front area of the binocular microscope objective 20 which is moved to a non-working position without hindering the normal use of the slit source projection device of the ophthalmic slit lamp microscope detector 20. The specific connection mode is between the additional floodlight projection device 10 and the ophthalmic slit lamp microscope detector 20, that is, the additional floodlight projection device 10 to the optical microscope of the ophthalmic slit lamp microscope detector 20 through the arm 14, and can be rotated left and right, and back and forth.

In FIG. 3, The ophthalmic slit lamp microscope detector 20 includes a platform moving assembly 21, a control handle 22, a bracket 23, a cheek bracket 24, a viewing assembly 25, a lighting assembly 26, and a digital assembly 27, The control handle 22 is provided on the right side of the platform mobile assembly 21, The bracket 23 is connected to the middle of the platform mobile assembly 21, The cheek support 24 is connected to the left side of the platform mobile assembly 21, The observation assembly 25 is attached to the illumination assembly 26 on the bracket 22, The additional floodlight projection device 10 is rotary connected to the rotating shaft on the bracket, The digital assembly 27 is connected below the observation assembly 25.

Figure 4:
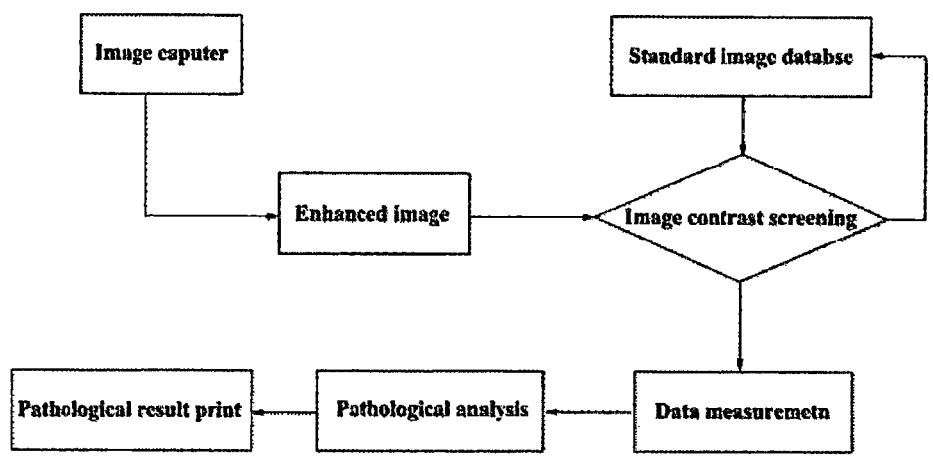
FIG. 4 is a working flow chart of the present invention.

As shown in FIG. 4, the workflow of the system of the present invention is as follows:

Step 1: A floodlight map graph with a special mesh is formed on the corneal surface to be detected by the additional floodlight projection device 10, and conventional detection of the detected cornea by the ophthalmic slit lamp microscope detector 20;

Step 2: The image acquisition device 30 performs optical image acquisition with the detected corneal surface formation, realizes the graph acquisition and forms the inspection data packet, and transmits the inspection data packet to the image analysis device 40;

Step 3: The image analysis device 40 filters and strengthens the graphics data in the inspection data packet and compares the standard graphics stored in the standard graphics library of the image analysis device 40, so as to extract the graphics with pathological changes, and then obtain the pathological examination results after the pathological analysis;

Step 4: The pathological examination result is printed using the result printing device 50.

The present invention is a platform according to an ophthalmic slit lamp microscope detector 20, If the original function of the ophthalmic slit lamp microscope detector 20 is not altered and restricted, The pathological shape that change on the surface of the cornea can be directly observed, And through the digital imaging acquisition function can obtain a higher resolution corneal surface mesh mapping image for independent intelligent procedural professional pathology analysis, Intelligent pathological observation means and judgment method under the principle of corneal surface deformation are realized, Thus, the professional technical means of pathological examination using the ophthalmic slit lamp microscope detector 20 were improved and expanded.

The technical scheme provided by the present invention is described in detail above. The principles and embodiment of the embodiments are only used to help understand the method of the invention and its core ideas. It should be noted that for those generally skilled in the art, several improvements and modifications of the invention may be made without departing from the principles of the invention, which also fall within the protection of the invention.

The invention disclosed an eye image analysis system based on an additional floodlight projection device and an ophthalmic slit lamp, Including a crack lamp microscope detector, an additional floodlight projection device, an image acquisition device, an image analysis device, The removable rotation of the additional floodlight projection device is attached to the ophthalmic slit lamp microscope detector, Used to form a floodlight map graph with special mesh lines on the surface of the cornea to be detected; The image acquisition device is used to acquire optical images by an optical aperture for the corneal surface, Form the check packet, And sent to the image analysis device; The image analysis device is used for flow processing, data filtering and comparative analysis of the acquired inspection packet, and pathological analysis, Results of the pathological examination were obtained. Its remarkable effect is: improve and expand the professional technical means of using the ophthalmic slit lamp microscope detector for pathological examination.

I claim:

1. An eye image analysis system based on an additional floodlight projection device and an ophthalmic slit lamp, comprising
   an ophthalmic slit lamp microscope detector, an additional floodlight projection device, an image acquisition device, and an image analysis device, wherein:
   a removable rotation of the additional floodlight projection device is attached to the ophthalmic slit lamp microscope detector for forming a floodlight map graph with a special mesh pattern on a surface of a cornea of a subject to be detected;
   the additional floodlight projection device includes an arm that is fixed to a side wall of an outer cover of the additional flood light projection device and the arm facilitates a rotational connection of the additional floodlight projection device with the ophthalmic slit lamp microscope detector;
   the additional floodlight projection device includes a projection structure and a projection light source, and the projection structure is configured to image a required projection pattern for ophthalmic inspection into the floodlight map graph with the special mesh pattern on the surface of the cornea of the subject to be detected;
   the projection light source adopts a reflective color filter flood light source arranged annular and collinear with a centerline of the projection structure;
   a center of the projection structure is opened axially with an optical aperture and the projection pattern is formed on a side wall of the optical aperture;
   the image acquisition device is used for optical image acquisition of the floodlight map graph formed on the surface of the cornea of the subject to be detected through the optical aperture, forming an inspection data packet, and transmitting the inspection data packet to the image analysis device; and
   the image analysis device is used to process the obtained inspection data package, data filtering contrast measurement, pathological analysis to obtain pathological examination results.

2. The eye image analysis system based on an additional floodlight projection device and an ophthalmic slit lamp according to claim 1, wherein the projection pattern can be rapidly replaced by a positioned slide pattern insert.

3. The eye image analysis system based on an additional floodlight projection device and an ophthalmic slit lamp according to claim 1, further comprising a result printing device that prints an analytical image and data measurement chart to provide clinical auxiliary pathological analysis based on a result of computer software assisted analysis obtained by an independent digital image acquisition processing analysis.

* * * * *